United States Patent [19]

Theeuwes

[11] Patent Number: 4,973,307
[45] Date of Patent: * Nov. 27, 1990

[54] METHOD FOR ADMINISTERING DRUGS TO A PATIENT

[75] Inventor: Felix Theeuwes, Los Altos, Calif.

[73] Assignee: Alza Corporation, Palo Alto, Calif.

[ * ] Notice: The portion of the term of this patent subsequent to Apr. 16, 2002 has been disclaimed.

[21] Appl. No.: 342,780

[22] Filed: Apr. 25, 1989

Related U.S. Application Data

[60] Division of Ser. No. 797,307, Nov. 12, 1985, Pat. No. 4,865,585, which is a continuation-in-part of Ser. No. 702,973, Feb. 19, 1985, Pat. No. 4,740,201, which is a division of Ser. No. 310,047, Oct. 9, 1981, Pat. No. 4,511,353, which is a continuation-in-part of Ser. No. 283,077, Jul. 13, 1981, abandoned, and a continuation-in-part of Ser. No. 664,802, Oct. 25, 1984, Pat. No. 4,790,820, which is a continuation-in-part of Ser. No. 576,929, Feb. 3, 1984, abandoned, which is a division of Ser. No. 377,831, May 13, 1984, Pat. No. 4,439,183, which is a continuation-in-part of Ser. No. 310,047, Oct. 9, 1981, Pat. No. 4,511,353, which is a continuation-in-part of Ser. No. 283,077, Jul. 13, 1981, abandoned, and a continuation-in-part of Ser. No. 588,165, Mar. 9, 1984, which is a continuation-in-part of Ser. No. 312,491, Oct. 19, 1981, Pat. No. 4,552,555, which is a continuation-in-part of Ser. No. 289,082, Jul. 31, 1981, abandoned.

[51] Int. Cl.$^5$ .............................................. A61M 37/00
[52] U.S. Cl. ..................................................... 604/85
[58] Field of Search .............................. 604/56, 82–85

[56] References Cited

U.S. PATENT DOCUMENTS

| Re. 25,129 | 2/1962 | Walter ................................. 604/252 |
|---|---|---|
| 911,523 | 2/1909 | Piers .................................. 604/92 X |
| 1,654,745 | 1/1928 | Miller ..................................... 604/80 |
| 2,682,268 | 6/1954 | Ryan et al. ...................... 604/252 X |
| 2,690,179 | 9/1954 | Fox ........................................ 604/87 |
| 2,849,256 | 8/1958 | Kowal ................................... 604/80 |
| 2,954,028 | 9/1960 | Smith .................................. 128/214 |
| 3,001,525 | 9/1961 | Hendricks ........................... 128/214 |
| 3,305,446 | 2/1967 | Bechtol et al. ........................ 167/72 |
| 3,332,114 | 5/1967 | Portnoy et al. .......................... 128/2 |
| 3,756,237 | 9/1973 | Chittenden et al. ................. 128/227 |
| 3,756,390 | 9/1973 | Abbey et al. ...................... 206/47 A |
| 3,760,984 | 9/1973 | Theeuwes .............................. 222/95 |
| 3,797,485 | 3/1974 | Urquhart .............................. 128/213 |
| 3,797,494 | 3/1974 | Zaffaroni ............................. 128/268 |
| 3,845,770 | 11/1974 | Theeuwes et al. ................... 128/260 |
| 3,847,150 | 11/1974 | Scheuermann ...................... 128/229 |
| 3,848,603 | 11/1974 | Throner ............................... 128/349 |
| 3,854,480 | 12/1974 | Zaffaroni ............................. 128/260 |
| 3,921,635 | 11/1975 | Gauthier .............................. 128/229 |
| 3,921,636 | 11/1975 | Zaffaroni ............................. 128/260 |
| 3,941,126 | 3/1976 | Dietrick et al. ...................... 128/214 |

(List continued on next page.)

FOREIGN PATENT DOCUMENTS

| 0059694 | 4/1982 | European Pat. Off. .............. 604/84 |
|---|---|---|
| 497181 | 9/1969 | Switzerland . |
| 982107 | 9/1963 | United Kingdom . |

OTHER PUBLICATIONS

Paxinos, J. & Samuels, T. M.; *Am J Hosp Pharm*, vol. 32, pp. 892–897, Sep. 1975.

Goodwin, H. N., *The American Journal of I. V. Therapy*, pp. 27–30, Dec.–Jan. 1975.

Masson, A. H. B., *Brit J. Anaesth.*, vol. 43, pp. 681–686, 1971.

Ferenchak et al., *Surgery*, vol. 70, No. 5, pp. 674–677, Nov. 1971.

*Primary Examiner*—J. L. Kruter
*Attorney, Agent, or Firm*—Edward L. Mandell; Steven F. Stone; Paul L. Sabatine

[57] ABSTRACT

A formulation chamber is disclosed comprising a wall surrounding a lumen containing means for delivering a beneficial agent. The chamber has an inlet for admitting a fluid into the chamber and an outlet for letting an agent formulation leave the chamber. The chamber is adapted for parenteral use including intravenous delivery for delivering an agent formulation to a patient.

1 Claim, 6 Drawing Sheets

U.S. PATENT DOCUMENTS

| | | | |
|---|---|---|---|
| 3,948,254 | 4/1976 | Zaffaroni | 128/127 |
| 3,976,068 | 8/1976 | Lindquist | 128/214 |
| 3,993,066 | 11/1976 | Virag | 128/260 |
| 3,993,072 | 11/1976 | Zaffaroni | 128/260 |
| 3,995,631 | 12/1976 | Higuchi | 128/260 |
| 4,061,141 | 12/1977 | Hydén et al. | 128/214 |
| 4,105,029 | 8/1978 | Virag | 128/260 |
| 4,116,646 | 9/1978 | Edwards | 55/159 |
| 4,177,256 | 12/1979 | Michaels et al. | 424/22 |
| 4,200,095 | 4/1980 | Reti | 128/214 |
| 4,203,439 | 5/1980 | Theeuwes | 128/260 |
| 4,217,894 | 8/1980 | Franetzki | 128/213 |
| 4,233,973 | 11/1980 | Shukla | 128/214 |
| 4,235,236 | 11/1980 | Theeuwes | 604/892 |
| 4,236,517 | 12/1980 | Langston et al. | 128/275 |
| 4,256,104 | 3/1981 | Muetterties et al. | 128/214 |
| 4,321,117 | 3/1982 | Kaetsu et al. | 204/159 |
| 4,323,457 | 4/1982 | Sun et al. | 210/645 |
| 4,465,471 | 8/1984 | Harris et al. | 604/56 |
| 4,548,598 | 10/1985 | Theeuwes | 604/85 |

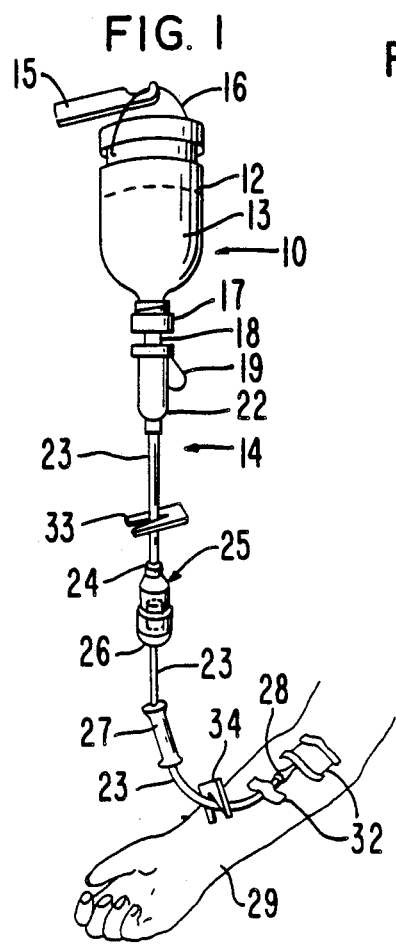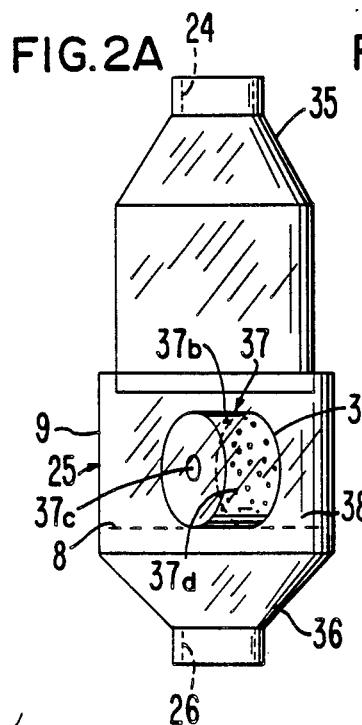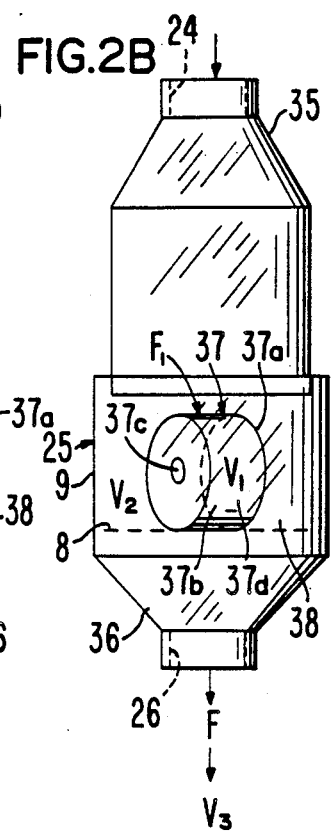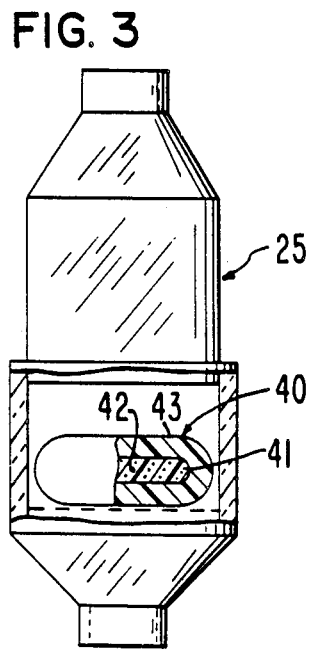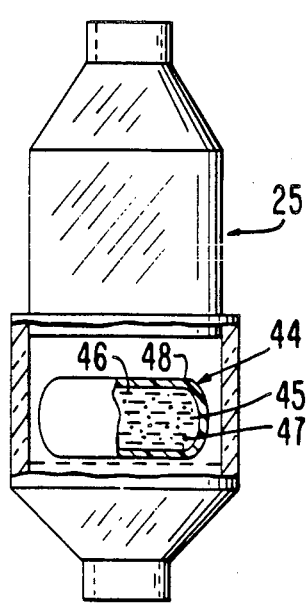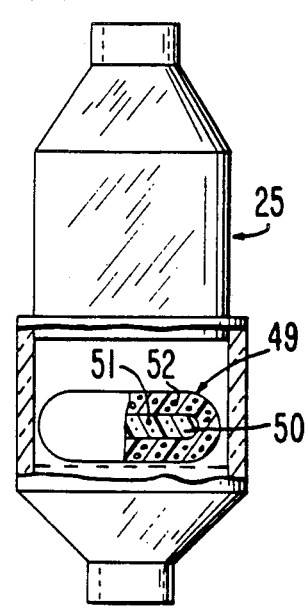

FIG_23
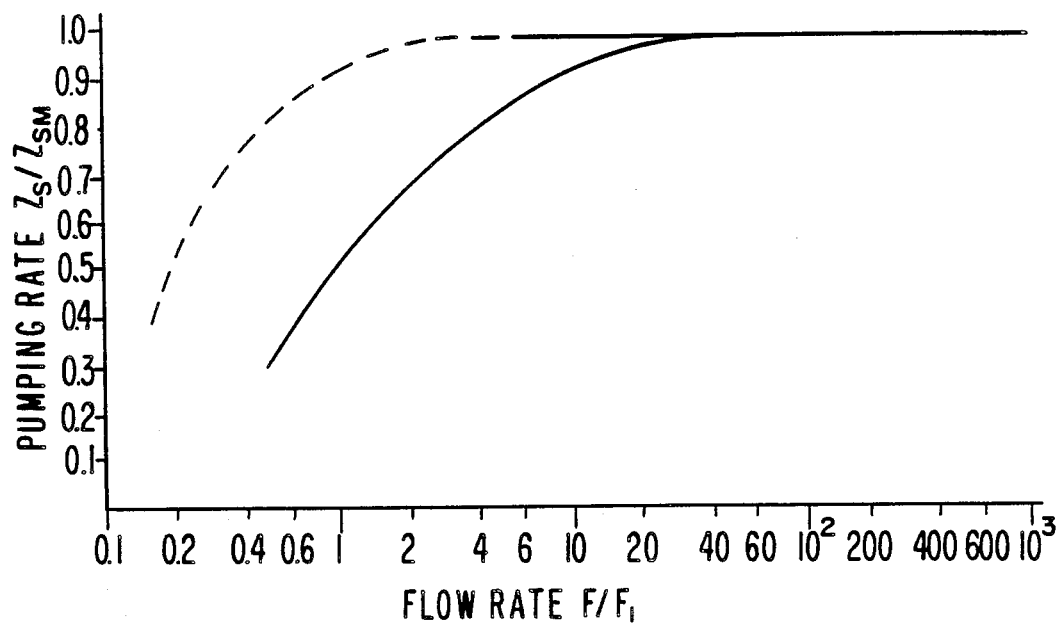
FIG_24
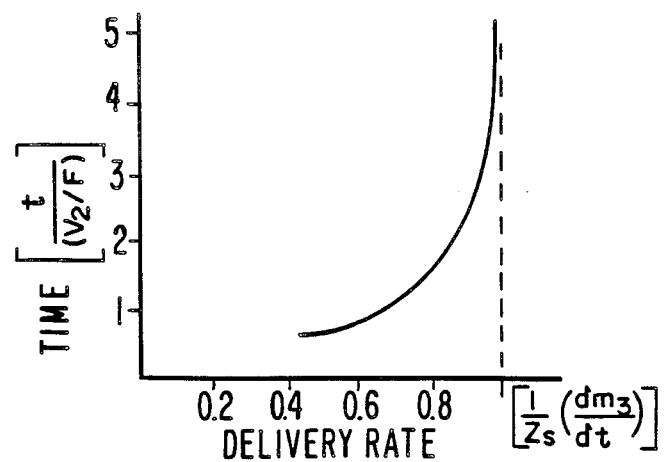

METHOD FOR ADMINISTERING DRUGS TO A PATIENT

CROSS-REFERENCE TO RELATED APPLICATIONS

This application is a division of, U S. patent application Ser. No. 06/797,307 filed Nov. 12, 1985, now U.S. Pat. No. 4,865,585 issued Sept. 12, 1989 which application Ser. No. 06/797,307 is a continuation-in-part of U.S. application Ser. No. 06/702,973 filed Feb. 19, 1985, now U.S. Pat. No. 4,740,210 issued Apr. 26, 1988 which application Ser. No. 06/702,973 is a division of U.S. application Ser. No. 06/310,047 filed Oct. 9, 1981, now U.S. Pat. No. 4,511,353 issued Apr. 16, 1985, which application Ser. No. 06/310,047 is a continuation-in-part of U.S. application Ser. No. 06/283,077 filed July 13, 1981 now abandoned.

This application Ser. No. 06/797,306 also is a continuation-in-part of U.S. application Ser. No. 06/664,802 filed Oct. 25, 1984, now U.S. Pat. No. 4,790,820 issued Dec. 13, 1988 which application Ser. No. 06/664,802 is a continuation-in-part of U.S. application Ser. No. 06/576,929 filed Feb. 3, 1984 now abandoned, which application Ser. No. 06/576,929 is a division of U.S. application Ser. No. 06/377,831 filed May 13, 1984, now U.S. Pat. No. 4,439,183 issued Mar. 27, 1984, which application Ser. No. 06/377,831 is a continuation-in-part of U.S. application Ser. No. 06/310,047 filed Oct. 9, 1981, now U.S. Pat. No. 4,511,353 issued Apr. 16, 1985 which application Ser. No. 06/310,047 is a continuation-in-part of U.S. application Ser. No. 06/283,077 filed July 13, 1981 now abandoned.

This application Ser. No. 06/797,307 also is a continuation-in part of U.S. application Ser. No. 06/588,165 filed Mar. 9, 1984, which application Ser. No. 06/588,165 is a continuation-in-part of U.S. application Ser. No. 06/312,491 filed Oct. 19, 1981, now U.S. Pat. No. 4,552,555 issued Nov. 12, 1985, which application Ser. No. 06/312,491 is a continuation-in-part of U.S. application Ser. No. 06/289,082 filed July 31, 1981 now abandoned. Two applications identified as Attorney's Docket No. ARC 319 Cont. 3 now U.S. application Ser. No. 07/338,691 filed Apr. 12, 1989 and as Attorney's Docket No. ARC 319 Div. 10 now U.S. application Ser. No. 07/342,840 filed Apr. 25, 1989 also are copending in the U.S. PTO.

The above applications are incorporated herein by reference and benefit is claimed of their filing dates. All of these applications are assigned to the ALZA Corporation of Palo Alto, Calif.

Other related cases assigned to ALZA Corporation are:. U.S. application Ser. No. 702,291 filed Feb. 15, 1985 now U.S. Pat. No. 4,746,103 issued Apr. 26, 1988; U.S application Ser. No. 702,293 filed Feb. 15, 1985 now U.S. Pat. No. 4,740,200 issued Apr. 26, 1988; U.S. application Ser. No. 702,292 filed Feb. 15, 1985 now U.S. Pat. No. 4,740,198 issued Apr. 26, 1988; U.S. application Ser. No 701,720 filed Feb 14, 1985 now U.S. Pat. No. 4,741,735 issued May 3, 1988; U.S. application Ser. No. 701,729 filed Feb. 14, 1985 now U.S. Pat. No. 4,740,197 issued Apr. 26, 1988; U.S. application Ser. No. 701,730 filed Feb. 14, 1985 now U.S. Pat. No. 4,740,199 issued Apr. 26, 1988; U.S. application Ser. No. 702,273 filed Feb, 15, 1985 now U.S. Pat. No. 4,586,922 issued May 6, 1986 and U.S. application Ser. No. 702,171 filed Feb. 15, 1985, now U.S. Pat. No. 4,741,734 issued May 3, 1988 all of which are divisions of U.S. application Ser. No. 319,047, now U.S. Pat. No. 4,511,353 issued Apr. 16, 1985; U.S. application Ser. No. 587,745 filed Mar. 9, 1984, now abandoned a continuation of U.S. application Ser. No. 310,047 now U.S. Pat. No. 4,511,353 issued Apr. 16, 1985; U.S. application Ser. No. 577,241 filed Feb. 3, 1984, now U.S. Pat. No. 4,548,598 issued Oct. 22, 1985; U.S. application Ser. No. 576,572 filed Feb. 3, 1984, now U.S. Pat. No. 4,521,211 issued June 4, 1985 and U.S. application Ser. No. 576,966 filed Feb. 3, 1984, abn., all of which are divisions of U.S. application Ser. No. 377,831, now U.S. Pat. No. 4,439,183 issued Mar. 27, 1984.

FIELD OF THE INVENTION

This invention pertains to an intravenous delivery system, and to a drug formulation chamber comprising an agent delivery system. The invention relates also to a method of administering intravenously an agent formulation and to a method for forming the agent formulation.

BACKGROUND OF THE INVENTION

The parenteral administration of medical liquids is an established clinical practice. The liquids are administered particularly intravenously, and the practice is used extensively as an integral part of the daily treatment of medical and surgical patients. The liquids commonly administered include blood and blood substitutes, dextrose solution, electrolyte solution and saline. Generally the liquids ar administered from an intravenous delivery system having a container suspended above the patient, with the liquid flowing through a catheter hypodermic needle set to the patient.

The administration of liquids intravenously is a valuable and important component that contributes to the optimal care of the patient; however, it does not provide a satisfactory means and method for administering concomitantly therewith a beneficial agent. Presently a beneficial agent is administered intravenously by (1) temporarily removing the intravenous system administering the agent to the patient followed by reinserting the intravenous system into the patient; (2) an agent is added to the liquid in the container and then carried by the flow of the liquid to the patient; (3) agent is added to a liquid in a separate container called a "partial fill" that is connected to the primary intravenous line through which line the agent is carried by the flow of liquid to the patient; (4) agent is contained in a piggyback vial into which is introduced an intravenous fluid, with the vial subsequently connected to the primary line through which the agent is administered to a patient, or, (5) agent is administered by a pump that exerts a force on a liquid containing agent for intravenously administering the liquid containing the agent. While these techniques are used, they have major disadvantages. For example, they often require preformulation of the agent medication by the hospital pharmacist or nurse, they require separate connections for joining the primary intravenous line that further complicates intravenous administration, the use of pumps can produce pressures that can vary at the delivery site and the pressure can give rise to thrombosis, and the rate of agent delivery to the patient often is unknown as it is not rate-controlled agent delivery, but delivery dependent on the flow of fluid administered over time. In view of this presentation it is apparent a critical need exists in the field of intravenous delivery for a rate-controlled means for administering a beneficial agent in intravenous delivery systems.

DISCLOSURE OF THE INVENTION

Accordingly, a principal object of this invention is to provide an intravenous delivery system comprising means for admitting an agent at a rate controlled by the means into an intravenous fluid for optimizing the care of a human whose prognosis benefits from intravenous delivery.

Another object of the invention is to provide an intravenous delivery system comprising an agent formulation chamber comprising an agent delivery device for admitting an agent at a rate controlled by the delivery device into an intravenous fluid for optimizing the care of a patient on intravenous therapy.

Another object of the invention is to provide an agent formulation chamber adapted for use with an intravenous delivery system and which chamber houses agent delivery means for admitting an agent at a controlled rate into an intravenous fluid admitted into the chamber.

Another object of the invention is to provide an intravenous therapeutic system comprising a container and a drug formulation chamber which chamber houses a device for delivering a drug at a rate governed by the device into a medical fluid that flows from the container into the chamber and then to a drug recipient.

Another object of the invention is to provide a intravenous therapeutic system comprising a container and a drug formulation chamber that houses a delivery system for forming an intravenously acceptable fluid drug formulation in situ at a rate governed by the system releasing the drug combined with controlling the volume of fluid flowing through the formulation chamber for mixing the drug with the intravenously acceptable medical fluid that flows from the container into the chamber and, hence, to a drug recipient.

Another object of the invention is to provide an intravenous formulation chamber equipped with a drug releasing member for (1) formulating an intravenously administrable fluid drug formulation in the formulation chamber by (2) adding a drug to an intravenous medical fluid that enters the chamber and is a pharmaceutically acceptable carrier for the drug at (3) a rate governed by the combined operations of the member releasing the drug and the rate of fluid flow through the chamber.

Another object of the invention is to provide a formulation chamber housing a delivery device containing a drug that forms on its release from the device a drug formulation with fluid that enters the chamber by the combined operations of the device releasing the drug and the rate of fluid flow through the chamber.

The invention concerns both an intravenous delivery system comprising an agent formulation chamber and the agent formulation chamber. The chamber contains an agent formulation, wherein (1) an agent originally present in a delivery means present in the chamber is released at a rate controlled by the delivery means. The agent on its release is formulated in situ with an intravenous fluid that enters the chamber with the agent released at a controlled rate that is preferably essentially independent of the volume rate of an intravenous fluid entering the formulation chamber, and the infused into a recipient. The expression, "delivery means", as used herein, generically denotes a means or a system for storing and delivering a beneficial agent at a rate controlled by the means to establish a beneficial or a therapeutic need. The means, in presently preferred embodiments, are designed and manufactured as an agent delivery device, which device also is a rate-controlled dosage form of the agent. The delivery device or dosage forms stores an amount of agent for executing a prescribed beneficial program, and it provides for the preprogrammed, unattended delivery of a beneficially or a therapeutically effective amount of the agent to produce a beneficial or therapeutic result. The delivery device, or the dosage form, are adapted for easy placement and retention in the formulation chamber, and they substantially maintain their physical and chemical integrity during their release history. The formulation chamber contain an agent formulation, wherein (2) agent in another embodiment is originally present in a pharmaceutical form that forms a fluid formulation in the chamber that is released from the formulation chamber by release rate means present in the formulation chamber. The expression, "beneficial agent" generically denotes a substance that produces a beneficial or a therapeutic result, such as a drug, a carbohydrate, and/or the like. The term, "fluid or liquid" denotes a fluid that can be administered parenterally, including intravenously, comprising pharmaceutically acceptable fluids that are also a pharmaceutically acceptable carrier for the agent. The invention also is an intravenous therapeutic system for administering a liquid drug formulation, wherein the liquid drug formulation is formulated in situ. The intravenous delivery system generically comprises in combination:

(a) a container for storing a pharmaceutically acceptable liquid carrier for the agent;

(b) an agent formulation chamber comprising: an inlet that permits communication with the container to let a liquid carrier flow from the container into the formulation chamber; and, an outlet through which the liquid exits the chamber;

(c) an agent delivery means in the chamber, which means is a rate-controlled dosage form of agent that is in communication with a liquid flowing through the chamber, and wherein, when in operation, the means releases the agent into the liquid at a predetermined rate that is substantially independent of the volume rate of liquid flow flowing through the chamber; or, (d) an agent in the chamber in a pharmaceutically acceptable form that is in communication with a liquid flowing through the chamber and a release rate film in the chamber, that release the agent and fluid from the chamber; and, (e) a conduit that communicates with the chamber outlet and extends to an infusion recipient site. The agent formulation chamber generally comprises means for housing and delivering an agent at a rate-controlled by the means over time, or an agent and a release rate film means that release agent from the chamber over time.

BRIEF DESCRIPTION OF THE DRAWINGS

In the drawings, which are not drawn to scale, but are set forth to illustrate various embodiments of the invention, the Figures are as follows:

FIG. 1 is a perspective view showing an embodiment of the invention comprising an intravenous delivery system in use;

FIGS. 2a and 2b are perspective views of an agent formulation chamber provided by the invention with the formulation chamber housing a means for delivering an agent which means is manufactured as an agent delivery device;

FIG. 3 is a view of an agent formulation chamber containing an agent delivery device comprising a agent release rate controlling membrane surrounding a reservoir containing agent;

FIG. 4 is a view of an agent formulation chamber containing a delivery device comprising a release rate controlling membrane surrounding a different reservoir containing agent;

FIG. 5 is a view of an agent formulation chamber containing a delivery device comprising a microporous membrane surrounding a reservoir containing agent;

FIG. 23 is a graph showing a typical relationship between the mass rate of agent administration and the volume flow rate of intravenous fluid to the patient that results from use of the invention; and, FIG. 24 is a graph that indicates the time required for the delivery rate to reach a steady state of delivery.

In the specification and drawings like parts in related Figures are identified by like numerals. The terms appearing earlier in the specification and in the description of the drawings are described hereafter in the disclosure.

MODES FOR CARRYING OUT THE INVENTION

Figure 6:
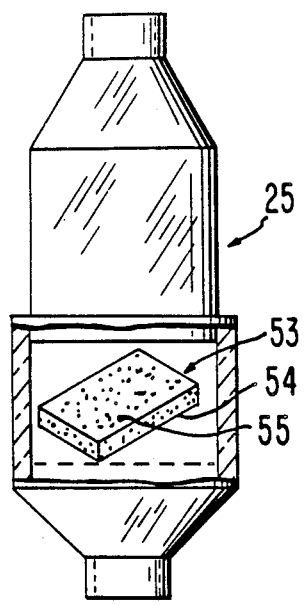
FIG. 6 is a view of an agent formulation chamber containing a delivery device comprising a matrix containing agent.

FIG. 1 illustrates one operative embodiment of the invention, comprising an intravenous delivery system, generally designated by the numeral 10. System 10 comprises a container 12 that contains a liquid 13 adapted for parenteral, including intravenous, administration, and an administration set, generally designated 14. The liquid 13 in container 12 will typically be a medical fluid, a sterile solution such as an aqueous solution of dextrose, saline, and electrolytes. It must be a pharmaceutical vehicle for intravenous administration and for an agent that is to be administered to a recipient. Container 12 is manufactured from glass or plastic, and preferably of the no air-tube vacuum type and, thus, it is used with an administration set that has an air inlet filter. Other types of containers such as the air-tube vacuum type, or the non-vented type can be used for the intended purpose. These alternative containers do not require an air filter in the administration set. Container 12 can be rigid, semi-rigid or flexible in structure, and it is usually adapted to be hung neck-down from a hanger 15 by a handle or strap 16 that connects or surrounds container 12. The neck of the container 12 is covered by a closure 17, generally made of rubber and air-tight.

Administration set 14 and container 12 are interconnected by piercing closure 17 with one end of a needle or hollow spike 18 attached to or formed as a part of administration set 14. Needle 18 is equipped with a side air vent 19. The other end of needle 18 is enlarged and fits snugly into a drip chamber 22. Drip chamber 22 traps air contained in the set and facilitates adjusting the flow rate of intravenous fluid 13 from container 12 a the flow proceeds drop wise. The outlet at the bottom of drip chamber 22 is connected to a first segment of tubing 23 which fits into inlet 24 of agent formulation chamber 25, the details of which are presented in subsequent figures. A second segment of tubing 23 connects to outlet 26 of agent formulation chamber 25 and leads to bacterial filter 27. A third segment of tubing 23 extends from filter 27 to a infusion agent receptor site, terminating in an adapted-needle assembly 28 that is inserted into a vein of a warm-blooded animal 29, shown as a human patient's arm. An affixation means 32, usually a piece of tape, holds adapter-needle assembly 28 firmly in place on the recipient's arm The administration set can also include a pair of tubing clamps 33 and 34 located on either side of formulation chamber 25 that may be used to govern or stop the flow rate of intravenous fluid through the intravenous therapy system.

Agent formulation chamber 25, as seen in FIGS. 2a and 2b, is the unique component of the intravenous delivery system. Agent formulation chamber 25 is sized and adapted for use in intravenous systems, it is self-contained, self-powered and amenable to low cost manufacturing. The use of the agent formulation chamber with an agent delivery means therein does not require any reconstitution or admixture prior to use. Agent formulation chamber 25, hereafter referred to as formulation chamber 25, in the illustrated embodiment, comprises a wall 9 that surrounds and defines an internal space 38. Chamber 25 has an inlet 24 adapted and sized for placing chamber 25 into an intravenous delivery system, and it has an outlet 26 also adapted and sized for placing the chamber in the system. Inlet 24 and outlet 26 are made for receiving tube 23. Chamber 25, is manufactured of glass, plastic or the like, and as illustrated it is made of a transparent material for illustrating its structure and a device housed therein. In the embodiment shown, chamber 25 comprises a pair of interfitting housing halves 35 and 36 for containing agent delivery device 37 within space or lumen 38. A retaining means 8 in housing 36 permits the passage of fluid, keeps delivery device 37 in lumen 38, and it also prevents device 37 from blocking outlet 26. Agent delivery device 37, in the illustrated embodiment is an osmotic device, a rate-controlled solid dosage form as described by patentee Felix Theeuwes in U.S. Pat. No. 3,845,770. The osmotic device 37, seen in opened section, comprises a semipermeable wall, 37a, such as cellulose acylate, cellulose diacylate, cellulose triacylate, cellulose acetate, cellulose diacetate or cellulose triacetate, that surrounds and forms a compartment 37b. A passageway 3c extends through semipermeable wall 37a and communicates compartment 37b and the exterior of osmotic device 37. Compartment 37b contains an agent formulation 37d, represented by dots, which agent formulation exhibits an osmotic pressure gradient across wall 37a of device 37 against an external fluid that enters chamber 25. The agent formulation can comprise an agent that exhibits an osmotic pressure gradient, or the agent formulation can comprise an agent mixed with an osmotically effective solute, such as sodium chloride, potassium chloride and the like, that exhibit an osmotic pressure substantially greater than the fluid in the chamber 25. In operation fluid that enters in the chamber 25 is imbibed through the semipermeable wall of the device into the compartment in a tendency towards osmotic equilibrium at a rate determined by the permeability of the wall and the osmotic gradient across the wall thereby producing a solution that is dispensed through the passageway at a rate controlled by the device over a prolonged period of time. The delivery of agent formulation 37d for homogeneously blending with fluid in chamber 25, is controlled by device 37, and its rate of delivery is independent of the rate of fluid flow, and the pH of the fluid in the chamber. Device 37 maintains its physical and chemical integrity throughout its releasing history. In other embodiments, not shown, chamber 25 can be manufactured as a one-piece unit with the delivery device therein, or chamber 25 can be manufactured with a closable entrance for admitting the delivery device. Additionally, another embodiment of the invention comprises chamber 25 simultaneously acting as a drip chamber while housing the agent delivery device. In this embodiment the agent formulation chamber-drip chamber is used to achieve a desired fluid drop rate. For example, the agent formulation chamber-drip chamber can have a fast drop rate for adults, or it can have a slower drop rate for pediatric use. The agent formulation chamber-drip chamber can be made with various sized inlets for controlling the rate of drip, or the drip can be controlled by a regulating clamp on the tubing conveying fluid thereto. The agent formulation chamber-drip chamber can deliver, for example, from 2 to 75 drops per milliliter over from 1 minute to 1 hour. More preferably, the therapist can adjust the rate of flow from 2 to 20 drops per minute, or for the need of the patient.

The rate performance of the delivery devices used in formulation chamber 25 for the purpose of the invention also can be described mathematically in terms of the physical and chemical composition of the agent release systems. Generally, delivery systems encompassed by this invention are those for which $Q_R \leq 0.1 Q_{KVO}$, where $Q_{KVO}$ is the flow of fluid required to maintain flow into the veins of an animal in which the flow path terminates by needle or catheter. This flow is referred to as the "keep vein open" rate, KVO, and it typically is for an adult patient about 10 to 20 drops per minute, or 0.5 to 1.0 ml per minute. $Q_R$ is the maximum rate of fluid flow needed for the delivery system to release agent in solution at its label rate. Thus, delivery systems for adult use require less than 0.05 to 0.1 ml/min to achieve stable delivery rate. Delivery systems for pediatric use will have a lower absolute limit, but still satisfy the general criterion of $Q_R \leq 0.1 Q_{KVO}$.

During operation of device 37 as seen in FIG. 2b, the mass delivery rate of agent from chamber 25 is given by the volume flow rate F expressed by equation (1), of fluid entering chamber 25, times the concentration of agent $C_2$, in the chamber with a volume $V_2$. In the chamber $V_2$ is the volume of the total chamber, less the volume $V_1$ of agent delivery device 37.

$$F = \frac{dV}{dt} \tag{1}$$

In the chamber it is assumed that lumen $V_2$ is stirred by fluid flow to achieve a uniform concentration $C_2$. The chamber is designed to produce a steady state mass flow rate $dm_3/dt$, expressed in equation (2), independent of flow rate F leaving the chamber and conveyed to an agent recipient, represented by volume $V_3$. The calculations presented here are:

$$\frac{dm_3}{dt} = \frac{dV}{dt} \cdot C_2 \tag{2}$$

performed to determine the flow regimen for which the intended end result can be achieved over time. The calculations are for an osmotic device, designated as 37, containing a mass of agent, m, at the start of a beneficial delivery program. During operation the device delivers at a zero order rate as given by equation (3).

$$\frac{dm_1}{dt} = K_1 \frac{A_1}{h_1} (\pi_1 - \pi_2) S_1 \tag{3}$$

wherein $K_1$ is the permeability of the wall of the delivery device to water, $A_1$ is the wall area of the device, $h_1$ is the thickness of the wall, $\pi_1$ is the osmotic pressure of saturated agent solution in the device, $\pi_2$ is the osmotic pressure of the solution in the lumen of the chamber at concentration $C_2$, and $S_1$ is the solubility of agent in volume $V_1$ in the device. The mass of agent $m_2$ in the lumen of the chamber at concentration $C_2$ is conveyed to the patient. The patient then has a total amount of agent infused of mass $m_3$ such that the mass balance at any time if given by equation (4):

$$m_{10} = m_1 + m_2 + m_3 \tag{4}$$

As a result the mass change in each compartment, the device, the chamber and the patient, is expressed by equation (5):

$$\frac{dm_1}{dt} + \frac{dm_2}{dt} + \frac{dm_3}{dt} = 0 \quad (5)$$

wherein $$\frac{dm_3}{dt} = FC_2 \quad (6)$$

since $$m_2 = V_2 \cdot C_2 \quad (7)$$

and it follows that $$\frac{dm_2}{dt} = V_2 \frac{dC_2}{dt} + C_2 \frac{dV_2}{dt} \quad (8)$$

as $$\frac{dV_2}{dt} = 0 \quad (9)$$

it follows that $$\frac{dm_2}{dt} = V_2 \frac{dC_2}{dt} \quad (10)$$

From equations (3), (5), (6) and (10), equation (11) follows:

$$V_2 \frac{dC_2}{dt} = K_1 \frac{A_1}{h_1} (\pi_1 - \pi_2) S_1 - FC_2 \quad (11)$$

wherein $h_2$ and $C_2$ are related through Van Hoff's law as shown by equation (12):

$$\frac{\pi_2}{\pi_1} = \frac{C_2}{S_1} \quad (12)$$

Equations (11) and (12) result in differential equation (13), from which $C_2$ follows as a function of time:

$$V_2 \frac{dC_2}{dt} = K_1 \frac{A_1}{h_1} \pi_1 \cdot S_1 - K_1 \frac{A_1}{h_1} \pi_1 C_2 - FC_2 \quad (13)$$

and when equation (14) is substituted therein, $$F_1 = K_1 \frac{A_1}{h_1} \cdot \pi_1 \quad (14)$$

equations (15) and (16) follow, $$V_2 \frac{dC_2}{dt} = F_1 S_1 - F_1 C_2 - FC_2 \quad (15)$$

$$\frac{dC_2}{dt} + \frac{(F_1 + F)}{V_2} C_2 = \frac{F_1 S_1}{V_2} \quad (16)$$

and for (16) the solution is given by equation (17):

$$C_2 = \frac{F_1 S_1}{F_1 + F} \left[ 1 - \exp - \left( \frac{F_1 + F}{V_2} \right) t \right] \quad (17)$$

Equation (17) indicates the time course in which $C_2$ attains its steady state value. The steady state value is given by (18), with the flow rate $$C_2 = \frac{F_1 S_1}{F_1 + F} \quad (18)$$

The flow rate into the patient is obtained form (17) and (2) as equation (19):

$$\frac{dm_3}{dt} = F \cdot \frac{F_1 S_1}{F_1 + F} \left[ 1 - \exp \frac{(F_1 + F)}{V_2} \cdot t \right] \quad (19)$$

Equation (19) leads to (1) the minimum flow rate $F_m$ needed to achieve a regimen independent of flow, and (2) the time it takes until the patient receives steady intravenous administration. The steady state flow rate achieved with the infuser is given by equations (20) or (21):

$$\left( \frac{dm_3}{dt} \right)_S = Z_s = F \cdot \frac{F_1 \cdot S_1}{F_1 + F} \quad (20)$$

$$Z_S = \frac{F_1 S_1}{1 + \frac{F_1}{F}} \quad (21)$$

and the maximum steady state flow rate is the steady state expressed by equation (22):

$$Z_{sm} = F_1 S_1 \quad (22)$$

the delivery rate from the delivery device. The steady state flow rate as a function of flow F is given by equation (23):

$$\frac{Z_S}{Z_{SM}} = \frac{1}{1 + \frac{F_1}{F}} \quad (23)$$

and graphically represented in FIG. 23, solid line, as a function of $F/F_1$, wherein it can be seen at high flow rates $F > F_1$, the agent delivery rate from the device is independent of fluid flow in the chamber.

Generally the volume flow rates from an osmotic device delivering at high rates, for example 100 mg/hr, are on the order of 0.05 to 0.2 ml/hr. The incoming fluid rate from a container containing a medical liquid, and referred to as the drip rates from an intravenous gravity feed system are in the range of from 1 to 400 ml/hr, and for these two ranges the total mass delivery rate is within 80% of the designed rate at all times.

The steady state rate of equation (20) can be expressed relative to the non-steady state of equation (19) by equation (24).

$$\frac{1}{Z_s} = \frac{dm_3}{dt} = 1 - \exp - \left[ \frac{(F_1 + F)}{V_2} \cdot t \right] \quad (24)$$

Under operating conditions $F_1 + F$, equation (24), can be expressed as equation (25), $$t = -\frac{V_2}{F} \cdot \ln\left[ 1 - \frac{1}{Z_s} \frac{dm_3}{dt} \right] \quad (25)$$

and $V_2/F$ is a characteristic time of the chamber. It is the time it takes to clear volume $V_2$ at incoming flow rate F. These systems are typically designed such that this time is small to reduce the start up time, and the dead volume $V_2$ usually is less than 1 ml. Thus, for the minimum flow rate of 1 ml/hr used in intravenous therapy, the characteristic time would be one hour. Accompanying FIG. 24 represents the time it takes to achieve any fraction of a steady state value in units of characteristic time, and generally indicating 80% of the steady state rate is achieved in 1.5 times the characteristic time.

FIG. 3 depicts agent formulation chamber 25, in opened section, containing another agent releasing device 40, or agent releasing unit, for delivering an agent into an intravenously acceptable fluid that enters chamber 25. Device 40 is illustrated in opened section and it comprises an inner mass transfer conductor 41, illustrated as a solid core and formed of a polymeric material such as cured polydimethylisoxane, with agent 42 dispersed therethrough. Surrounding mass transfer conductor 41 is an agent release rate controlling membrane 43, preferably formed of a polymeric material, such as polyethylene. Both conductor 41 and membrane 43 are permeable to the passage of agent 42 by diffusion, that is, agent can dissolve in and diffuse through conductor 41 and membrane 43. However, the permeability of conductor 41 is greater than that of membrane 43, and membrane 43 thus acts as the rate controlling member for agent release from device 40. Device 40 maintains its physical and chemical integrity throughout the period of agent delivery. Agent delivery device 40 is disclosed in U.S. Pat. No. 3,845,480.

FIG. 4 illustrates the agent formulation chamber, with a section of its wall removed, housing delivery device 44 for delivering an agent at a rate controlled by device 44 into a fluid that enters chamber 25. Device 44 is seen in opened section and it comprises a reservoir 45 formed of a liquid mass transfer conductor 46 such as a medical oil, a liquid carrier, permeable to the passage of agent, containing agent 47 such as the drug phenobarbital. Reservoir 45 is surrounded by a wall 48 formed of an agent or drug release rate controlling material permeable to the passage of agent 47, such as a polyolefin. The rate of passage of agent 47 is lower than the rate of passage through conductor 46, so that agent release by wall 48 is the agent release rate controlling step for releasing agent 47 from device 44. Device 44 maintains its physical and chemical integrity throughout its agent release history. Agent delivery device 44 is disclosed in U.S. Pat. No. 3,993,073, which patent is incorporated herein by reference.

FIG. 5 illustrates agent formulation chamber 25, with a part of its wall removed, housing another device 49 for delivering an agent into a liquid that enters chamber 25 for forming an intravenously acceptable agent formulation. Device 49 is seen in opened section and it comprises a wall 52 surrounding a reservoir 50 containing agent 51. The reservoir is formed of a solid carrier permeable to the passage of agent such as cured polydimethylsiloxane containing the drug diazepam. Wall 52 is formed of a microporous material, the pores of which contain an agent release rate controlling medium permeable to the passage of agent 51, for example, formed of a microporous polymer made by coprecipitation of a polycation and a polyanion. The release of agent 51 is controlled by device 49, which device maintains its physical and chemical integrity during the period of time it is in chamber 25. Device 49 is disclosed in U.S. Pat. No. 3,9093,072, which patent has been incorporated herein by reference.

FIG. 6 is a view of formulation chamber 25 having part of its housing removed and housing device 53 for delivering an agent into a medical fluid that enters chamber 25 for forming in situ an intravenously acceptable agent formulation solution. Device 53 comprises a matrix 54 containing agent 55 distributed therethrough. Matrix 55 is formed from a polymeric material that is non-erodible, that is, it keeps its physical and chemical integrity over time, and it is permeable to the passage of agent 55 by the process of diffusion. The rate of agent release from the matrix is determined by the rate the agent dissolves in and passes through the matrix by diffusion, so that from the matrix it is the agent release rate controlling step. The matrix can possess any shape such as rod, disc and the like that fits into chamber 25. The polymers include polyolefins such as polyethylene containing muscle relaxants and the like. Materials useful for manufacturing the devices are disclosed in U.S. Pat. No. 3,921,636.

Figure 7:
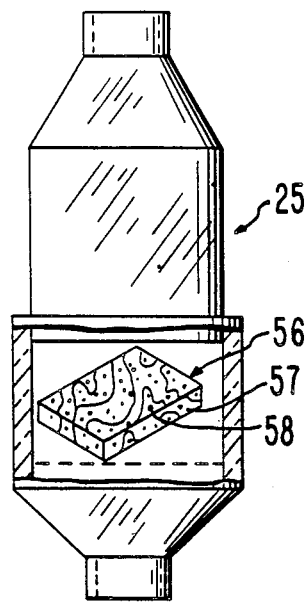
FIG. 7 is a view of an agent formulation chamber containing an agent delivery device comprising a microporous matrix containing an agent.

FIG. 7 is a view of agent formulation chamber 25, in opened view, housing device 56 for delivering an agent into a fluid that enters chamber 25. Device 56 is seen in opened section, and it is formed of a microporous polymeric material 57 containing agent 58 distributed therethrough. Matrix 57 is formed of a non-toxic, inert polymer, that is non-erodible and has a plurality of micropores for releasing agent at a controlled rate to fluid entering chamber 25. Microporous materials useful for the present purpose are disclosed in U.S. Pat. Nos. 3,797,494 and 3,948,254.

Figure 8:
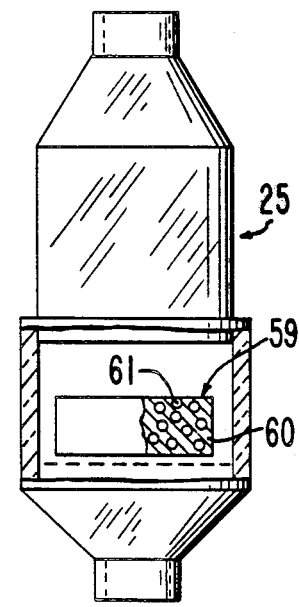
FIG. 8 is a view of an agent formulation chamber containing a delivery device comprising depots of agent.

FIG. 8 illustrates agent formulation chamber 25, in opened view, housing device 59 for delivering an agent into a medical fluid that enters chamber 25. Device 59 is seen in opened section and it comprises deposit of agent solute 61 dispersed in and surrounded substantially individually by a polymer 60 that is impermeable to the passage of agent solute and permeable to the passage of fluid that enters chamber 25. Agent or a medication solute 61 exhibits an osmotic pressure gradient across the polymer against fluid that enters chamber 25. Agent 61 is released at a controlled rate by fluid from the chamber being imbibed through the polymer into the depots to dissolve the solute and generate a hydrostatic pressure in the depots, which pressure is applied against the wall of the depots thereby forming apertures that release the agent at a controlled rate over time. Polymer 60 is non-erodible, and device 59 can be shaped as a matrix, a rod, a disc, or like shapes. Procedures and materials useful for manufacturing osmotic bursting delivery systems are described in U.S. Pat. No. 4,177,256.

Figure 9:
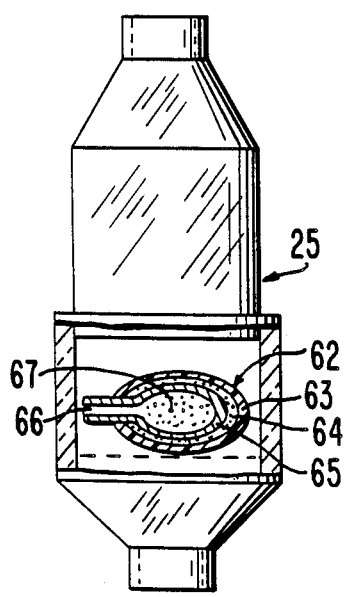
FIG. 9 is a view of an agent formulation chamber containing a delivery device comprising a housing and driving member surrounding a flexible container.

FIG. 9 illustrates agent formulation chamber 25, in opened view, containing a delivery system 62 manufactured as a delivery device useful for delivering an agent into a medically acceptable fluid passing through chamber 25. Device 62 is seen in opened view and it comprises an exterior wall 63 formed of a semipermeable polymer permeable to fluid and substantially impermeable to the passage of agents and solutes. A layer 64 of an osmotically effective solute, for example sodium chloride, is deposited on the inner surface of wall 63. Solute layer 64 surrounds an inner container 65 formed of a flexible materials that is impermeable to solute and agent. Container 65 has a passageway 66 for delivering an agent 67 into a fluid in chamber 25. Device 62 dispenses agent by fluid permeating from chamber 25 through the outer wall 63 to continuously dissolve solute 64 in a tendency towards osmotic equilibrium, thereby continuously increasing the volume between wall 63 and container 65. This increase causes container 65 to continuously collapse and dispense agent 67 from device 62 at a controlled rate through passageway 66 to fluid passing through chamber 25. Osmotically powered agent dispensing devices are disclosed in U.S. Pat. Nos. 3,760,984 and 3,995,631.

Figure 10:
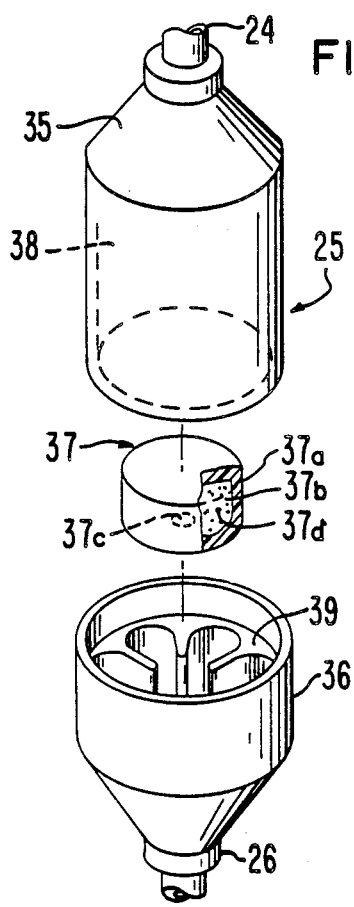
FIG. 10 is an embodiment of the invention illustrating an agent formulation chamber in fragmentary view.
Figure 11:
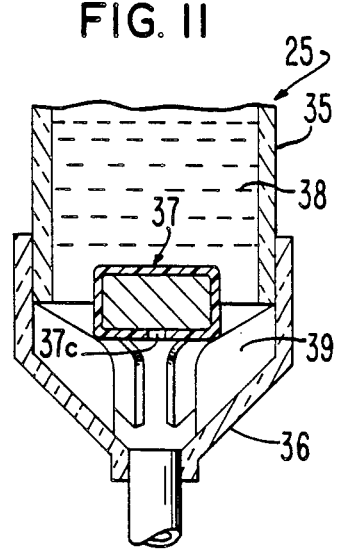
FIG. 11 is a sectional, fragmentary view of the parts of the embodiment showing in FIG. 10.
Figure 14:
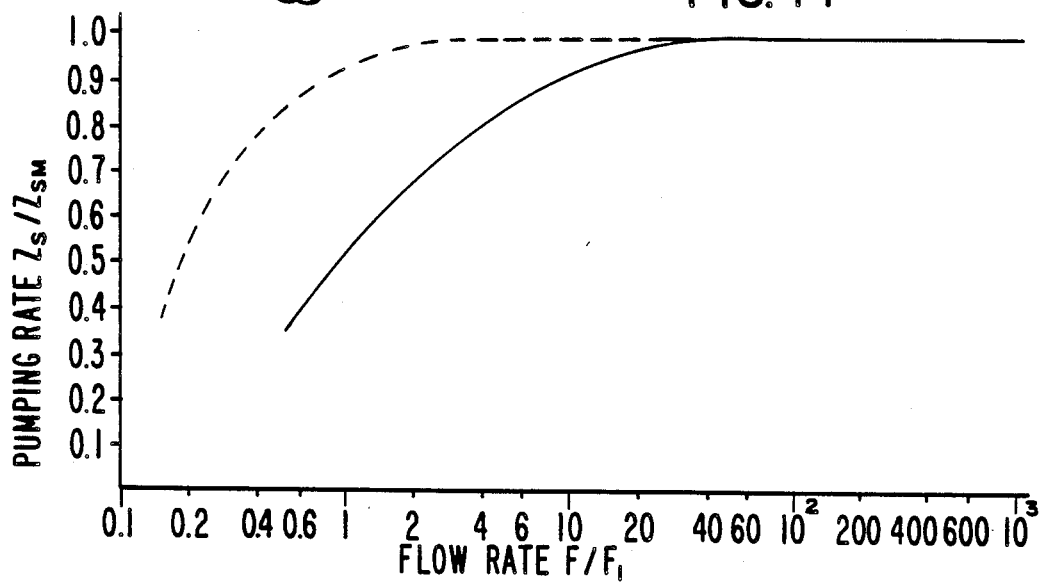
FIG. 14 is a view of a formulation chamber housing a delivery system comprising a multiplicity of tiny timed pills.

In FIGS. 10 and 11 another chamber 25 provided by the invention is seen composed of a pair of interfitting housing halves 35 and 36 and a rate controlled solid agent or drug dosage form 37 contained within the lumen 38 of chamber 25. The chamber inlet 24 is in this embodiment the cone-shaped of housing half 35, and the chamber outlet 26 is the cone-shaped end of half 36. The inside perimeter of half 36 has a series of downwardly inclined flutes 39 on which dosage form 37 rests. The dosage form is supported by the flutes above the outlet, and is thus kept from blocking the outlet. Dosage form 37 is an osmotic, rate-controlled dosage form as described above and in U.S. Pat. No. 3,845,770, which disclosure is incorporated herein by reference. In the illustrated embodiment, dosage form 37 has passageway 3c oriented in the direction of fluid flow through chamber 25 for lessening the incidence of membrane polarization and to produce release rates practically unaffected by effluent agent. In this operation the release pattern is seen in FIG. 23 as represented by the dashed lines. Another osmotic agent delivery device, now shown, that can be positioned in chamber 25 is disclosed by patentee Felix Theeuwes in U.S. Pat. No. 4,111,202, which patent is incorporated herein by reference. The device of this patent comprises a semipermeable wall that surrounds a first and second compartment with the first compartment containing an agent and the second compartment containing an osmotically effective solute that exhibits an osmotic pressure gradient across the semipermeable wall. In this device the compartments are separated by a flexible membrane and the device has a passageway that communicates with the compartment containing the agent for its delivery from the device. This device, when in operation, delivers agent by imbibing fluid from the infuser into the first compartment to form a solution containing agent and into the second compartment to form a solution containing the solute which continuously fill the second compartment and expands the membrane into the first. The agent is delivered through the passageway by the combined actions of the first and second compartments at a controlled rate over a period of time, For this delivery device, like the device described above, the mass rate of agent released by the device is substantially independent of the volume flow of intravenous fluid to the patient as it is instead controlled by the mass release of agent form the dosage device. This relationship is shown in FIG. 14 in solid line. In FIG. 23 the rate of release from the device when passageway 3c is directed in the path of liquid flow is illustrated in dashed lines.

Agent administration that is independent of intravenous fluid flow rate is extremely advantageous as careful control of the volume flow rate of intravenous fluid through the formulation chamber is not required. Hence, repeated adjustment of the flow by medical personnel, or the use of expensive, automated flow monitors is not needed. The operation also has all the advantages that are associated with the fact that the formulation of agent and intravenous fluid is carried out automatically in situ within the chamber. Moreover, since the chamber can be positioned within the intravenous therapeutic system when needed, the separation of the agent and the intravenous fluid until administration provides significant stability and handling advantages. The present invention also eliminates the need to have the agent formulated into a parenteral solution by a pharmacist, and it also eliminates the need for the agent to be packaged separately from the intravenous fluid container. Another advantage provided by this invention is that the agent dosage delivery device is compatible with conventional sterilization techniques that are commonly used to sterilize intravenous therapy systems, so the agent formulation chamber, including the agent delivery device, may be incorporated into the entire intravenous system at the time of manufacture and sterilized therewith.

Figure 12:
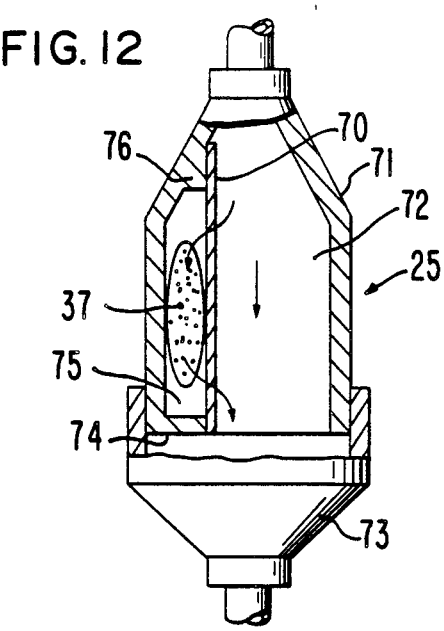
FIG. 12 is an enlarged, partly sectional view of another formulation chamber.

FIG. 12 illustrates another agent formulation chamber designated 25. In this chamber the rate-controlled dosage delivery device is not in direct path of the intravenous fluid flow through chamber 25. In this embodiment chamber 25 includes a pair of hollow interfitting housing halves 71 and 73. Housing half 71 has an inlet opening or its cone shaped end for tubing 23. The inner surface of half 71 carries a pair of integral flanges 74 and 76 that together with a thin microporous membrane 70 define an enclosed pocket 75 inside the lumen 72 of chamber 25. An agent delivery device 37 is contained within the pocket. Device 37 is, as described above, a complete rate-controlled form and it may additionally act in combination with membrane 70 to enhance the control of agent into passing fluid. Such combinations, in which an element of chamber is used with a delivery device, are intended to be within the phrase rate-controlled delivery as used herein. In such combinations membrane 70 can serve as a rate-controlling barrier that regulates the rate at which the agent enters the mainstream of intravenous fluid flow through the chamber. As device 37 is a complete rate-controlled form, the membrane acts as a supplemental barrier or as a means for confining the device so that it does not block the entrance or exit of chamber 25. Membrane 70 permits the passage of fluid so that as intravenous fluid fills and passes through the chamber, which flow is represented by the straight arrow in FIG. 12, water from the fluid will diffuse, represented by curved arrows, through the pores of the membrane into the pocket and motivates device 37 to release drug. The released agent will pass from the pocket through the membrane into the mainstream flow through chamber 25. The rate at which the agent will enter the mainstream will depend on its concentration in the solution within the pocket, the surface area of membrane 70, and the rate of passage of the membrane to agent. In any event, that rate is independent of the overall flow rate of intravenous fluid through chamber 25. Accordingly the agent is formed in situ within chamber 25 and it is administered to the patient at a rate that is dependent upon the characteristics of the device. The microporous membrane 70 may be useful also to prevent agent particles from entering the flow path, and for providing an extra margin of safety against microorganisms, in the event any may have survived the sterilization procedure for the system.

Figure 13:
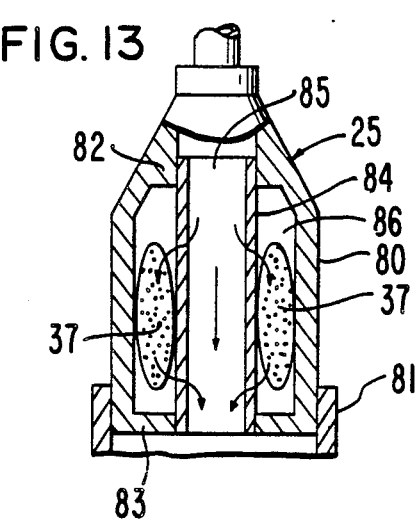
FIG. 13 is an enlarged, partly sectional view of still another embodiment of an agent formulation chamber housing a delivery device.

FIG. 13 shows another agent formulation chamber, generally designated 25, in which the dosage form is not in the direct path of the intravenous fluid flow through the chamber. The chamber is particularly adapted to hold a plurality of the same or different delivery devices. The chamber, like those shown in the other figures, includes a pair of hollow, interfitting housing halves 80 and 81 that have an inlet opening and outlet opening, now shown, at their respective ends. The inside surface of half 80 carries a pair of radial flanges 82 and 83 that extend entirely around the inner circumference of the half. These flanges, together with a tubular microporous membrane 84 that is attached at its ends to the flanges, divides the lumen of the chamber into a main intravenous flow path 85 and an outer concentric pocket 86. A plurality of agent delivery units 37 are contained within the pocket. Membrane 84 and pocket 86 functions in the same manner as membrane 70 and pocket 75 of FIG. 12. That is, as intravenous fluid flows through the chamber, water from the fluid diffuses through the membrane into pocket 86 and causes the device to release agent. The agent then diffuses from the pocket through the membrane and into the mainstream of the intravenous fluid flow. In instances in which the devices are different, it may be desirable to divide pocket 86 into a plurality of pockets, one for each device. This may be accomplished with impermeable axial partitions, now shown, that extend between the inner surface of the half, the membrane, and the two flanges. In such instances it may be also desirable to have membrane 84 formed from segment of different microporous materials, each segment covering a separate pocket. In this manner different release rates of different agents into the passing intravenous fluid may be effected.

In FIG. 14, formulation chamber 25 is illustrated with a section removed for depicting the inside of the chamber. The chamber is light weight, disposable and indicated for use in patients requiring intravenous administration of a fluid containing a beneficial agent, such as an intravenously administrable drug. In FIG. 14 formulation chamber 25 comprises a wall body 87 of tube shape and it has a pair of caps 88 and 89 for forming a closed chamber containing fluid and a delivery system. Caps 88 and 89 fit chamber 25 and they ar preferably made of self-sealing rubber through which a needle or a hollow spike can be inserted, or they can have an integrally formed tubular extension 90 and 91 for receiving an incoming tube. Hollow tube member 90 and 91 are preferably round for receiving a tube that slides into, or slides over the member. Formulation chamber 25 is made of a material that is moisture proof, impermeable to microorganisms, does not adversely affect a drug or a delivery system, is permeable to ionizing rays, and adapted to house a delivery system and incoming fluids.

The delivery system depicted in formulation chamber 25 comprises a multiplicity of tiny timed pills 92 for the controlled delivery of an agent, including drug, into a fluid entering chamber 25. The tiny pills are seen in detail in opened section pill 93, and they comprise a core of drug 94 surrounded by a wall 95 formed of a release rate controlling material. Tiny pills 92 can also comprise encapsulated different drug present as separate drug particles. Tiny pills 92 can also comprise drug in an opened porous matrix, or tiny pills 92 can also comprise microparticles present in a single core matrix or microparticles present in a separate supporting matrix for each microparticle. The tiny times pills 92 provide a high membrane surface area for achieving high release rates of agent for forming an agent solution. The tiny pills release drug at a rate of at least 1 nanograms per hour over time into incoming fluid to form the intravenous solution. The total number of tiny pills 92 in formulation chamber 25 can be varied as an added means for regulating the amount of agent made available for forming an agent solution. The materials forming wall 95 can be selected from materials that release drug 94 by different physical-chemical mechanisms. These mechanisms include erosion, diffusion and osmosis mechanisms. Wall 95 when releasing drug by osmosis releases drug by bursting. Drug 94 in this embodiment is present in the form of an osmotic solute, such as a therapeutically acceptable salt, and it exhibits an osmotic pressure gradient across wall 95 against an external fluid that enters the formulation chamber. The membrane materials used to form wall 95 are those permeable to the passage of an external fluid and substantially impermeable to the passage of drug. Typical materials include a member selected from the group consisting of cellulose acylate, cellulose diacylate, cellulose triacylate, cellulose acetate, cellulose triacetate, and the like. The osmotic wall can be coated around the drug in varying thickness by pan coating, spray-pan coating, Wurster fluid air suspension coating, and the like. The wall is formed using organic solvents, including methylene chloride-methanol, methylene chloride-acetone, methanol-acetone, ethylene dichlorideacetone, and the like. Osmotic wall forming materials, procedures for forming the wall and osmotic bursting procedures are described in U.S. Pat. Nos. 2,799,241, 3,952,741, 4,014,344 and 4,016,880.

Wall 95 of tiny pills 92 in another embodiment can be made of a drug releasing material. That is, drug 94 dissolves in the wall or through pores within the wall and passes through the wall or through said proes at a controlled rate by diffusion over time. Exemplary material useful for forming a diffusional wall or a wall with pores include ethylene-vinyl acetate copolymer, ethyl cellulose, polyethylene, cross-linked polyvinyl pyrrolidone, vinylidene chloride-acrylonitrile copolymer, polypropylene, silicone, and the like. The wall can be applied by techniques described above, and materials suitable for forming wall 95 are described in U.S. Pat. Nos. 3,938,515, 3,948,262, and 4,014,333.

Wall 95 of tiny pills 92 can be made of bioerodible material that bioerodes at a controlled rate and releases drug 94 to the fluid in chamber 25. Bioerodible materials useful for forming wall 95 include polycarboxylic acid, polyesters, polyamides, polyimides, polylactic acid, polyglycolic acid, polyorthoesters, and polycarbonates that erode to form intravenously acceptable end products. These polymers and procedures for forming wall 81 are disclosed in U.S. Pat. Nos. 3,811,444, 3,867,519, 3,888,975, 3,971,367, 3,993,057 and 4,138,344. The amount of drug present in a tiny timed pill generally is about 10 ng to 50 mg, and the number of tiny pills in a chamber is about 10 to 1000, preferably at least 50 to 150. The tiny pills comprising the wall and the inner core of drug have a diameter of at least 100 microns and, in a presently preferred embodiment, a diameter of at least 2000 microns. The tiny pills can have one or more coatings of wall-forming materials thereon. The beneficial agent on release by the delivery system is formulated in situ, mixed, added, dissolved, suspended, carried and/or the like, in or by the fluid into a physical-chemical form acceptable for parenteral administration, including intravenous administration. Chamber 25 optionally is equipped with a support 96 for the tiny pills. Support 96 can be a film having release rate properties and made of a polymer that releases drug from chamber 25. Support 96 can be a microporous polymeric membrane, a sintered glass support, a perforated grid and/or the like.

Figure 15:
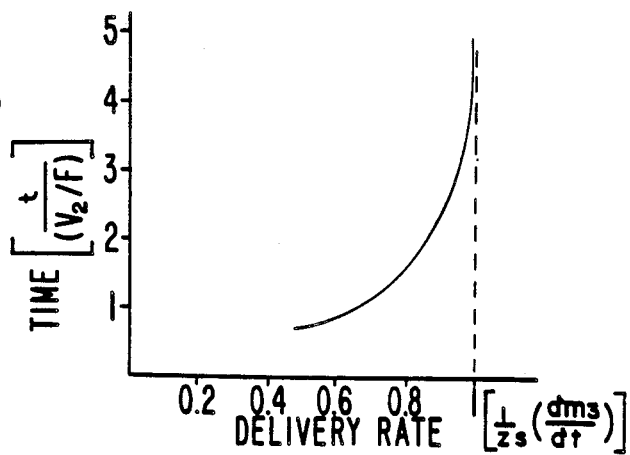
FIG. 15 is a view of a formulation chamber seen in opened section depicting the chamber housing a delivery system comprising a plurality of tiny capsules containing a beneficial agent.

FIG. 15 illustrates a formulation chamber 25 comprising a wall 97 surrounding a lumen 98 having an inlet 99 and an outlet 100. Chamber 98 houses a plurality of tiny capsules 101 further seen in opened section in capsule 102. Capsule 102 comprises a wall 103 surrounding a mass of liquid drug 104. The tiny capsules can be made by co-acervation technique consisting essentially of forming three immiscible phases, a liquid manufacturing phase, a core material phase and a coating phase. The coating phase is deposited as a liquid on the core material and rigidized usually by thermal, cross-linking or similar techniques to form tiny microcapsules. The capsules made by this technique have an average particle size of from several tenths of a micron to 5,000 microns and in some embodiments a larger tiny capsule can be used therein. Particle size, however, is not critical in the practice of this invention. Suitable techniques for preparing tiny microcapsules are reported by Bungenberg de Jone and Kass, *Biochem. Z.*, Vol. 232, pp 338 to 345, 1931; *Colloid Science*, Vol. 11, "Reversible System," edited by H. R. Kruyt, 1919, Elsever Publishing Co., Inc., New York; *J. Pharm. Sci.*, Vol 59, No. 10, pp 1,367–1,376; and *Pharmaceutical Science*, Remington, Vol. XIV, pp 1,676–1,677, 1970, Mack Publishing Co., Easton, Pa. Formulation chamber 25 also contains a film 104 that supports the tiny capsules and which film can also serve a a means for regulating the release of drug solution from formulation chamber 25.

Figure 16:
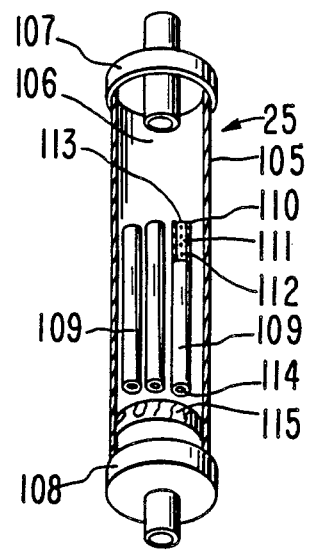
FIG. 16 is a view of a formulation chamber housing a delivery system comprising a multiplicity of hollow fibers filled with beneficial agent.

FIG. 16 illustrates a formulation chamber 25 comprising a wall 105 that surrounds an internal lumen 106 with an inlet end 107 and an outlet end 108. Chamber 25 houses a multiplicity of hollow fibers 109, with one fiber seen in opened section comprising a wall 110, that can be formed of a semipermeable polymer, a diffusional polymer, a microporous polymer, a lamina, or a laminate of two or more lamina surrounding a lumen 111 containing drug 112. The hollow fibers provide a large exposed surface area for concomitantly releasing a large amount of agent into the formulation chamber. The hollow fibers can have a length of a few millimeters to many centimeter or longer, a diameter or a millimeter or larger, and the chamber houses at least one hollow fiber to several hundred or more. The hollow fibers have openings at each end, 113 and 114; can be produced from non-cellulosic polymers using melt spinning techniques using shaped spinnerettes. Hollow fibers can also be produced by spinning an organic solvent cellulosic solution into certain regenerants, n-octanol where the solvent is dialkylacylamide, and n-hexanol where the solvent is dimethyl sulfoxide. The hollow fibers can be filled with drug by using a solution of drug injected into one opened end of the fiber, by soaking in a drug solution, and the like. The hollow fibers can release an agent by diffusion, dialysis, osmotic leaching and like techniques. The amount of agent released from the fibers further can be regulated by selecting the dimensions and number of hollow fibers housed in the formulation chamber. A procedure for manufacturing hollow fibers is disclosed in U.S. Pat. No. 4,086,418. Formulation chamber 25 optionally contains a support 115 for holding the fiber which support permits the passage of drug formulation from chamber 25.

Figure 17:
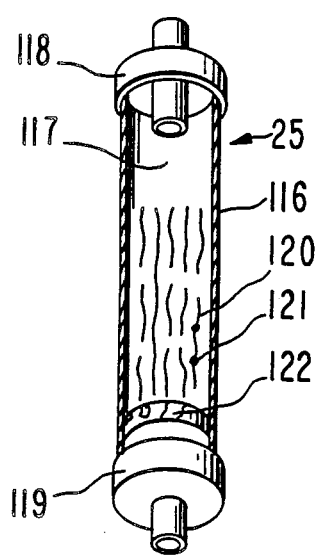
FIG. 17 is a view of a formulation chamber housing a delivery system comprising a plurality of solid fiber filled with beneficial agent.

FIG. 17 illustrates formulation chamber 25, seen in opened section, and it comprises a wall 116 that surrounds a lumen 117 with an inlet 118 and an outlet 119 for admitting and exiting fluid from chamber 25. Chamber 25 houses a multiplicity of fibers 120 containing drug 121, represented by dots. The fibers 120 forming the drug deliver system can be of natural or synthetic origin, and they can have a wide variety of structures, such as solid, semi-solid, porous, and the like; a variety of geometric shapes such as round, oval, square, trilobal; various lengths and cross-sections, and the like. The fibers can function effectively as a reservoir by having drug dispersed therethrough. Suitable fibers can be made by conventional fabrication techniques. For example, fiber material and drug may be dissolved in a solvent, extruded through small holes of a die and then solidified by standard melt spinning, wet spinning, or dry spinning techniques. In another embodiment the fibers can be produced by pumping a melt of fiber and drug through a spinneret.

With such a method, fiber diameter may be varied from a few tenths to a micron to a millimeter or so by down-drawing, or by up-drawing techniques. The lumen of the chamber can house fibers of mixed denier. The fibers forming the reservoir can be filled, saturated, or semi-filled with drug by immersing, soaking, or the like, and permitting the desired amount of drug to transfer into the fibers. Other techniques and drugs for forming fibers are disclosed in U.S. Pat. Nos. 3,228,887 and 3,921,636. The materials forming the fibers can be polyolefins, polyamides, polyurethanes, cellulosic materials, and the like. Fiber procedures are set forth in *Encyclopedia of Science and Technology*, Vol. 5, pp 263–276, 1971, published by McGraw Hill Co., New York. Chamber 25 also contains a membrane 122 for supporting the fibers and it can be formed of a diffusional or porous polymer for cooperating with the fibers for regulating the amount of drug solution infused into a patient.

Figure 18:
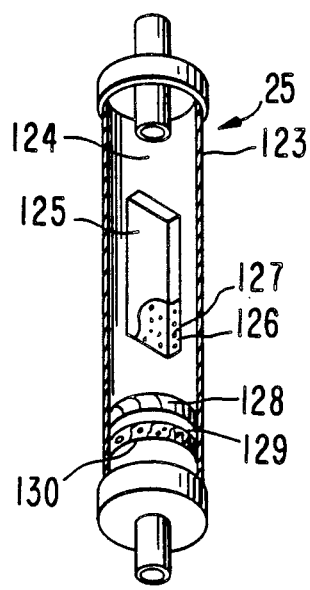
FIG. 18 is a view of a formulation chamber housing a delivery system comprising a drug delivery system consisting of a bioerodible polymer housing beneficial agent.

FIG. 18 illustrates a formulation chamber 25 having a section of its wall 123 removed for depicting the internal space 124 as a means for housing a beneficial agent delivery system 125. System 125 comprises a reservoir formed of an erodible polymer, and a section 126 is removed for illustrating agent 127 dispersed therein. The erodible polymer can be a member selected from the group including polyorthoesters, polyorthocarbonates, polyglycolic acid, polylactic acid, polyacetals, polyketals, polyamino acids, and the like. Procedures and erodible polymers are disclosed in U.S. Pat. No. 4,180,646; in *Int. J. of Pharmaceutics*, Vol. 7, pp 1–18, 1980; in *Biodegradables and Delivery Systems for Contraception*, Chapter 2, edited by E. S. E. Hafex and W. A. A. Van Os, published by G. K. Hall, Boston, 1980. Chamber 25 also can have a release rate controlling polymeric film 128 such as cellulose acetate, or the like, and a filter 129. Filter 129 is a conventional filter with a pore 130 having pore size of 0.1 micron to 5 micron, and more preferable 0.22 micron or 0.45 micron, for removing bacterial and unwanted matter from flowing solution, thereby aiding in maintaining a sterile solution.

Figure 19:
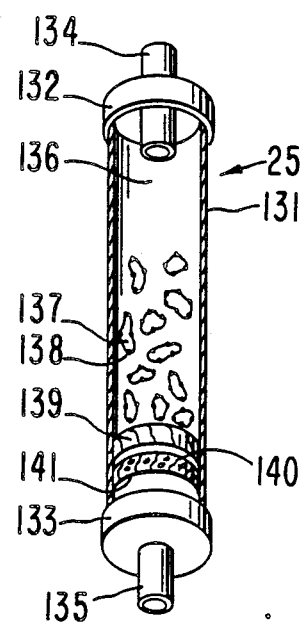
FIG. 19 is an opened view of a formulation chamber housing a plurality of ion-exchange member with active agent ionically bonded thereto.

FIG. 19 illustrates a formulation chamber 25 in opened view comprising a wall 131 surrounding an internal space closed at its inlet end with a cap 132 and at its outlet end with cap 133. Cap 132 has a tube receiving member 134 and caps 133 has a tube receiving member 135 for letting a fluid into and out of formulation chamber 25. Formulation chamber 25, in its internal space 136, houses a delivery system comprising a plurality of ion exchange resin particles 137 having a drug 138 ionically attracted thereto. The particles, and the like, can vary in size, usually from 10 to 350 mesh. The resins can be homopolymers, copolymers, derivatives thereof, or cross-linked resins. Typical resins include ion exchange resins such as cross-linked styrene-divinyl benzene, and the like, having drug 138 ionically bonded thereto. Active drug 138 is released from resin 137 into fluid that enter the formulation chamber to form in the chamber a drug solution for administering to a patient. The combination comprising the intravenous formulation chamber and the drug ion exchange member is a useful improvement in intravenous therapy. The improvement in forming the drug fluid formulation in situ comprises governing the combined operation of physical-chemical operation that continuously occur simultaneously in the formulation chamber. That is, the rate of drug fluid formulation is governed by the rate of release of ion drug from the ion exchange combined with the rate of fluid flow and the drug exchangeable ion concentration in the fluid to yield an intravenously administrable fluid drug formulation. Chamber 25 also ca house a film 139 that releases the drug formulation and a filter 140 having pores 141 for preventing bacteria and unwanted matter from leaving the formulation chamber. The ion exchange resins are disclosed in U.S. Pat. No. 4,203,440.

The invention, as exemplified by the above figures, provides that agent delivery devices containing various amounts of an agent or an amount of drug can be placed into the formulation chamber. The device can contain from about 1 mg to 5 g of agent or more, in, for example, 1 to 7 or more dosage units. The device can release agent at a rate of 10 ng/hr up to 2 g/hr into the chamber having a volume capacity of least 2 ml up to 250 ml, through which intravenous fluid flows at a rate of 1 ml/hr up to 20 ml/hr or higher. The term drug is represented by heparin, isoproterenol, and the like.

Agent formulation chamber 25 is a unique component of the parenteral, including intravenous, delivery system both as the chamber alone and in combination with the system. In another embodiment of the invention formulation chamber 25 contains an intravenously administrable beneficial agent, and the use of formulation chamber 25 with agent therein does not require any reconstitution or admixture prior to use. The agent in chamber 25 can be in any pharmaceutical state that forms an agent formulation with the fluid that enters the chamber. Exemplary pharmaceutically acceptable forms include solid, crystalline, microcrystalline, particle, pellet, granule, powder, tablet, spray-dried, lyophilized, and compressed forms that undergo disintegration and dissolution in the presence of an intravenous fluid such as compressed particles, compressed powders, compressed granules, friable layers of agent, and the like. Agent formulation chamber 25 generally will store an amount of agent for executing a prescribed therapeutic or beneficial program. That is, an amount of agent for the preprogrammed, unattended delivery of a therapeutically or a beneficially effective amount of the agent to produce a therapeutic or a beneficial result.

Agent formulation chamber 25 generally can house from about 5 milligrams to 20 grams of agent, or more. In the embodiments wherein chamber 25 contains a beneficial agent in the immediately above mentioned pharmaceutically acceptable forms, chamber 25 optionally is equipped with a release rate controlling membrane, for example a microporous polymeric membrane, or the like, that governs the rate of release of agent solution from chamber 25. The membrane can rest on a sintered glass support, not shown, integrally made into chamber 25; the membrane can be sealed adhesively to the inside wall of chamber 25; fused thereto; be supported by wall of the chamber pinched inwardly; on a rim in the chamber; or it can be supported or suitably fixed to an end cap of chamber 25. Optionally chamber 25 can be equipped with a release rate controlling membrane at its inlet for governing fluid flow into chamber 25.

Figure 20:
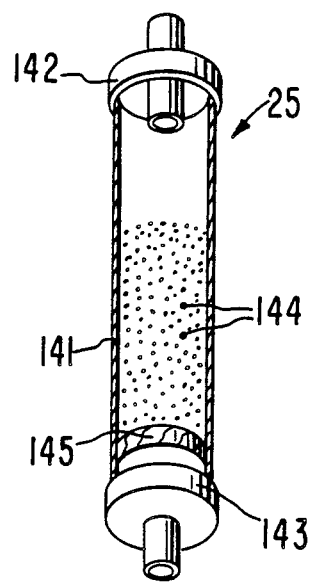
FIG. 20 is an opened view of a beneficial agent formulation chamber comprising a beneficial agent and a flow controlling membrane for governing the rate of fluid passage and the accompanying rate of drug passage through the chamber.
Figure 21:
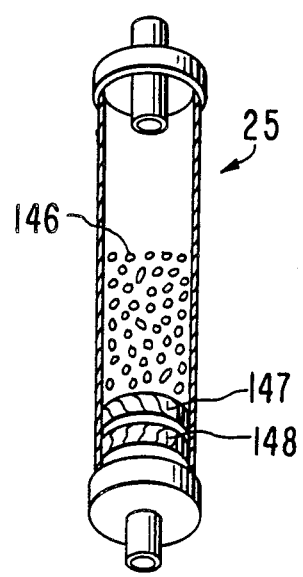
FIG. 21 is an opened view of a formulation chamber comprising a beneficial agent, a flow controlling membrane, and a filter.
Figure 22:
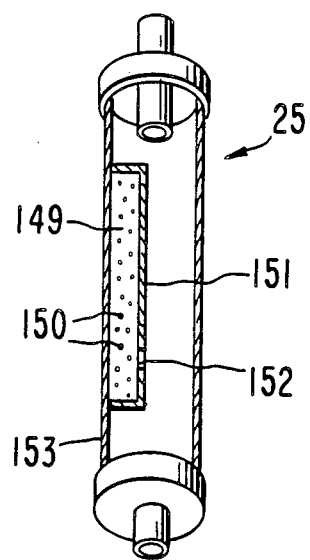
FIG. 22 is an opened view of a formulation chamber manufactured with an agent containing compartment.

FIGS. 20 through 22 illustrate formulation chambers with a section removed for depicting the inside of the chambers containing a pharmaceutically acceptable form. In FIG. 20, chamber 25 comprises a wall 141 with a section removed at ends 142 and 143. Chamber 25 contains agent 144 that is soluble in intravenously acceptable fluids, and a film 145 formed of a material for controlling the flow of fluid and agent from chamber 25. Film 145 in a preferred embodiment is formed of an agent release rate controlling polymer, such as a microporous polymer like a polycarbonate, a semipermeable polymer like cellulose acetate, or a diffusional polymer like ethylene-vinyl acetate copolymer. The polymeric film according to the mode of the invention is used in a presently preferred embodiment for governing the rate of release of solution containing agent from chamber 25, that is, agent release and fluid flow through chamber 25. Chamber 25 is illustrated with a film at its exit and, optionally, it can have a film at its inlet.

FIG. 21 illustrates a formulation chamber 25, in open view, comprising agent 146 in particle form, a release rate controlling film 147 such as cellulose acetate or the like, and a filter 148. Filter 148 is a conventional filter with a pore size of 0.1 micron to 5 micron, or more, preferably 0.22 micron or 0.45 micron, for removing bacteria and unwanted matter from the flowing solution, thereby aiding in maintaining a sterile solution.

FIG. 22 illustrates formulation chamber 25 made with an internal pocket 149 defining an area for containing agent 150, for example, the drug ephedrine sulfate. Pocket 149 is formed of a wall 151 made of a material such as a diffusional, semipermeable, or a microporous polymer that permit the passage of medical fluid into pocket 149 and agent solution formed therein from pocket 149. In an embodiment, when wall 151 is a semipermeable polymer that divides chamber 25, it can be provided with a delivery orifice 152 to dispense the agent solution into chamber 25. Wall 151 is joined by adhesive, heat sealing, or the like, to wall 153 of chamber 25. Wall 153 is made of a material substantially impermeable to the passage of agent, medical fluid and agent solution formed therein. In operation fluid enters chamber 25 and then into pocket 149 wherein it forms a solution containing the agent that passes into chamber 25 and them is administered therefrom to a recipient. The system in FIG. 22 allows regulation of fluid flow independently from agent delivery. Delivery is governed by the mass transport characteristics of membrane 151, and fluid flow is governed by a resistance element, for example, a flow regulator in the fluid path.

The novel and useful invention provides a parenteral, including intravenous, delivery system, a formulation chamber comprising means for supplying a beneficial agent, and a method for obtaining precise control of agent release with a parenteral delivery system for administration to a warm-blooded animal. While there has been described and pointed out features of the invention as applied to presently preferred embodiments, those skilled in the art will appreciate that various modifications, changes, additions and omissions in the invention illustrated and described can be made without departing from the spirit of the invention.

I claim:

1. A method for administering a drug formulation and a parenteral fluid to a warm-blooded animal, the method comprising:

(a) admitting intravenously into an animal in need of the drug formulation and a parenteral fluid a delivery member connected to an intravenous therapeutic system, the system comprising:

(1) a container of a pharmaceutically acceptable parenteral fluid that is a carrier for the drug;
   (2) a tube in fluid communication with the container for the flow of fluid therethrough;
   (3) a drug formulation chamber comprising a volume of 2 ml to 250 ml connected to the tube, the formulation chamber comprising:
      (i) a wall surrounding a lumen;
      (ii) an inlet in the wall for receiving the tube and for admitting fluid into the formulation chamber;
      (iii) a drug delivery device in the chamber, which device comprises from 1 mg to 5 g a beneficial drug that is released in a dose of at least 10 ng per hour at a rate controlled by the delivery device into fluid in the formulation chamber and at a rate independent of the rate of fluid flow through the chamber;
      (iv) an outlet in the wall for receiving the tube for the flow of drug formulation from the formulation chamber; and, (b) administering the drug formulation to the warm-blooded animal in a therapeutically effective amount.

* * * * *

UNITED STATES PATENT AND TRADEMARK OFFICE
CERTIFICATE OF CORRECTION

PATENT NO. : 4,973,307
DATED : November 27, 1990
INVENTOR(S) : Felix Theeuwes

It is certified that error appears in the above-identified patent and that said Letters Patent is hereby corrected as shown below:

Claim 1, in column 22, in line 13, insert after "5 g" ----of---.

Signed and Sealed this

Eighteenth Day of June, 1991

*Attest:*

*Attesting Officer*

HARRY F. MANBECK, JR.

*Commissioner of Patents and Trademarks*